(12) United States Patent
Allmendinger et al.

(10) Patent No.: US 10,321,881 B2
(45) Date of Patent: Jun. 18, 2019

(54) GENERATING HIGH-RESOLUTION CT IMAGES WITH SPECTRAL INFORMATION

(71) Applicant: Siemens Healthcare GmbH, Erlangen (DE)

(72) Inventors: Thomas Allmendinger, Forchheim (DE); Steffen Kappler, Effeltrich (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 16 days.

(21) Appl. No.: 15/819,326

(22) Filed: Nov. 21, 2017

(65) Prior Publication Data
US 2018/0146938 A1 May 31, 2018

(30) Foreign Application Priority Data
Nov. 29, 2016 (DE) .................. 10 2016 223 698

(51) Int. Cl.
*A61B 6/00* (2006.01)
*A61B 6/03* (2006.01)
(Continued)

(52) U.S. Cl.
CPC ............ *A61B 6/4241* (2013.01); *A61B 6/032* (2013.01); *A61B 6/482* (2013.01); *A61B 6/5205* (2013.01);
(Continued)

(58) Field of Classification Search
CPC ....... A61B 6/4241; A61B 6/032; A61B 6/482; A61B 6/5205; A61B 6/4266;
(Continued)

(56) References Cited

U.S. PATENT DOCUMENTS 9,316,745 B2 * 4/2016 Noshi .................. A61B 6/4241
9,662,078 B2 * 5/2017 Berglund ............. A61B 6/4233
(Continued)

FOREIGN PATENT DOCUMENTS

DE 102015206127 A1 10/2016
WO WO-2004071299 A1 8/2004

OTHER PUBLICATIONS

Picha Shunhavanich et al: "Lossy Compression of Projection Dara from Photon Counting Detectors"; 4th International Conference on Image Formation in X-Ray Computed Tomography, pp. 467-470, XP055461354,; 2016.
(Continued)

*Primary Examiner* — Michael S Osinski
(74) *Attorney, Agent, or Firm* — Harness, Dickey & Pierce, P.L.C.

(57) ABSTRACT

A method is for generating CT image data with spectral information from an examination region of a patient. According to an embodiment, the examination region is exposed to polychromatic X-radiation. Data from the examination region, including a first projection measurement data record and at least one second projection measurement data record, is captured via a photon counting detector. At least one second projection measurement data record with reduced resolution is generated based upon the at least one second projection measurement data record. The first and at least one second projection measurement data records are then transmitted to an image generation unit. Finally, the resolution of the first projection measurement data record is transferred onto the at least one second projection measurement data record with reduced resolution and/or an image data record based on the at least one second projection measurement data record with reduced resolution. A system is also disclosed.

20 Claims, 4 Drawing Sheets

(51) Int. Cl.
*G01T 1/29* (2006.01)
*G06T 11/00* (2006.01)
*G01N 23/046* (2018.01)

(52) U.S. Cl.
CPC ......... *G01N 23/046* (2013.01); *G01T 1/2928* (2013.01); *G06T 11/005* (2013.01); *G06T 2211/408* (2013.01)

(58) Field of Classification Search
CPC .. A61B 6/4233; A61B 6/5235; G01N 23/046; G01N 23/087; G01T 1/2928; G01T 1/2985; G06T 11/003–11/008; G06T 2207/10081; G06K 9/342
See application file for complete search history.

(56) References Cited

U.S. PATENT DOCUMENTS

| | | | | |
|---|---|---|---|---|
| 9,861,331 | B2* | 1/2018 | Wang | A61B 6/488 |
| 9,872,662 | B2* | 1/2018 | Raupach | A61B 6/032 |
| 2006/0081785 | A1 | 4/2006 | Heismann et al. | |
| 2006/0280281 | A1* | 12/2006 | Flohr | A61B 6/4241 378/5 |
| 2010/0328313 | A1* | 12/2010 | Zamyatin | G06K 9/342 345/440 |
| 2011/0121163 | A1* | 5/2011 | Kang | G01N 23/087 250/252.1 |
| 2013/0148873 | A1* | 6/2013 | Arenson | G06T 11/005 382/132 |
| 2013/0251220 | A1 | 9/2013 | Kraft | |
| 2013/0301799 | A1* | 11/2013 | Kang | A61B 6/5258 378/62 |
| 2013/0307923 | A1* | 11/2013 | Inglese | A61B 6/025 348/36 |
| 2014/0119507 | A1* | 5/2014 | Oh | A61B 6/52 378/62 |
| 2015/0043796 | A1 | 2/2015 | Rigie et al. | |
| 2015/0192681 | A1* | 7/2015 | Cho | G01T 1/161 250/366 |
| 2015/0363939 | A1* | 12/2015 | Choi | A61B 6/5264 382/132 |
| 2016/0192895 | A1* | 7/2016 | Han | A61B 6/481 600/431 |
| 2016/0203620 | A1* | 7/2016 | Zou | A61B 6/032 378/19 |
| 2016/0300368 | A1 | 10/2016 | Flohr et al. | |
| 2017/0258412 | A1* | 9/2017 | Daerr | A61B 6/032 |
| 2018/0098746 | A1* | 4/2018 | Kato | A61B 6/585 |
| 2018/0156742 | A1* | 6/2018 | Cao | G01T 1/366 |
| 2018/0158215 | A1* | 6/2018 | Pang | G06T 11/005 |
| 2018/0188391 | A1* | 7/2018 | Daerr | G01T 1/24 |
| 2018/0267175 | A1* | 9/2018 | Sano | G01T 1/2002 |
| 2018/0300909 | A1* | 10/2018 | Tamura | G06T 11/008 |
| 2018/0315224 | A1* | 11/2018 | Lou | G06T 11/006 |
| 2019/0018153 | A1* | 1/2019 | Cao | A61B 6/42 |

OTHER PUBLICATIONS

Search Report for European Patent Application No. 17197258.1 dated Apr. 6, 2018.

* cited by examiner

GENERATING HIGH-RESOLUTION CT IMAGES WITH SPECTRAL INFORMATION

PRIORITY STATEMENT

The present application hereby claims priority under 35 U.S.C. § 119 to German patent application number DE 102016223698.9 filed Nov. 29, 2016, the entire contents of which are hereby incorporated herein by reference.

FIELD

At least one embodiment of the invention generally relates to a method for generating CT images with spectral information. At least one embodiment of the invention also generally relates to an image generation system. At least one embodiment of the invention further generally relates to a computer tomography system.

BACKGROUND

Two-dimensional or three-dimensional image data is often generated with the aid of advanced imaging methods, said data being used to visualize an examination object that is depicted and also for further applications.

The imaging methods are often based on the capture of X-radiation, wherein so-called projection measurement data is generated. Projection measurement data can be acquired with the aid of a computer tomography system (CT system), for example. In the case of CT systems, a combination of X-ray source and X-ray detector arranged opposite each other on a gantry usually rotate around a measurement chamber in which the examination object (subsequently referred to as the patient without thereby restricting general applicability) is situated. In this case, the center of rotation (also referred to as the "isocenter") coincides with a so-called system axis z. During the course of one or more rotations, the patient is penetrated by X-radiation from the X-ray source, projection measurement data or X-ray projection data being captured by the X-ray detector situated opposite.

The generated projection measurement data is dependent on the design format of the X-ray detector in particular. X-ray detectors usually have a plurality of detection units which are generally arranged in the form of a regular pixel array. The detection units each generate a detection signal for X-radiation which strikes the detection units, said X-radiation being analyzed at specific time points in respect of intensity and spectral distribution in order to draw conclusions about the examination object and generate projection measurement data.

For the purpose of detecting the X-radiation, use can be made of so-called quantum counting detectors, for example. In the case of quantum counting or photon counting X-ray detectors, the detection signal for X-radiation is analyzed in respect of the intensity and the spectral distribution of the X-radiation in the form of count rates. The count rates are provided as output data of a so-called detector channel, which is assigned to a detection unit in each case. In the case of quantum counting detectors or photon counting detectors having a plurality of energy thresholds, each detector channel usually generates a set of count rates per projection on the basis of the respective detection signal of the detection unit. The set of count rates in this case may comprise count rates for a plurality of different energy threshold values, in particular energy threshold values which are checked concurrently. The energy threshold values, and the number of energy thresholds to which an energy threshold value is assigned in each case, are usually preset as signal analysis parameters for capturing the projection.

The application of such photon counting detectors in the context of clinical computer tomography allows spectral imaging to take place using polychromatic radiation sources in typically 2 to 4 spectral ranges. The previously cited energy threshold values to be checked correspond to these ranges. Such dual-energy or multi-energy CT methods allow the identification and quantification of different materials such as e.g. iodine and bones in the patient.

In addition to this, it is possible using photon counting detectors to achieve a considerably higher detector resolution, which is approximately two to five times the resolution of conventional CT detectors.

Use of the two advantages of a quantum counting detector, i.e. the spectral imaging and the higher resolution, implies a huge increase in the volume of data to be processed. Said increase relates to both the volume of raw data resulting from an image recording and the subsequent processing of the raw data to produce image data. Due to the transfer of the spectral information, the data rate in the case of 2 to 4 channels increases by a factor of 2 to 4. As a result of increasing the spatial resolution by a factor of 2 to 5, the data rate increases by a factor of 22 to 52. Therefore the volume of data under the cited conditions can increase by a factor of 8 to 100. In addition to this, the so-called frame rate, i.e. the frequency with which the individual image recordings are recorded in the case of a CT image recording from different directions, must be adapted to the higher spatial resolution (i.e. increased) in order that the higher resolution can be used, thereby further increasing the volume of data.

One possibility for limiting the volumes of data during spectral CT imaging is to reduce the detector resolution via so-called pixel fusing, i.e. combining of a plurality of pixels. Alternatively, it is also possible to limit the number of spectral ranges in order to reduce the volumes of data transferred. A further possibility for limiting the volumes of data is to reduce the zoning of a detector. However, the cited measures require the user to decide in advance which properties are particularly important for the imaging. For example, it must be decided how important a maximum resolution or the availability of spectral information or the size of the image region to be depicted are to the examination. Settings must be made accordingly in advance of the image recording, in order to obtain the desired imaging parameters. However, optimization of one of the cited properties is made at the expense of the others and vice versa.

SUMMARY

The inventors have recognized that a problem therefore exists wherein if the advantages of photon counting detectors are fully utilized, the volumes of data to be transferred and processed are significantly increased. Therefore, the costs involved in designing the necessary hardware are likewise significantly increased.

This problem is solved by at least one embodiment of a method for generating CT images with spectral information; at least one embodiment of an image generation system and/or at least one embodiment of a computer tomography system.

According to at least one embodiment of the inventive method for generating CT image data with spectral information from an examination region of a patient, the examination region is exposed to polychromatic X-radiation. Spectrally resolved projection measurement data from the examination region is then captured via a photon counting detector having a plurality of energy thresholds. The spectrally resolved projection measurement data comprises a first projection measurement data record, which is assigned to a first energy threshold, and at least one second projection measurement data record, which is assigned to at least one second energy threshold.

On the basis of the at least one second projection measurement data record, at least one second projection measurement data record with reduced resolution is generated. This procedure takes place in a detector-based manner, i.e. in a data reduction unit which is attached to the detector and follows the movement of the detector. The first projection measurement data record and the at least one second projection measurement data record with reduced resolution are then transmitted to an image generation unit. The image generation unit is situated outside the system that follows the rotational movement of the gantry.

By virtue of at least one embodiment of the inventive method, the transfer of the projection measurement data records can advantageously be carried out at least partly with reduced resolution and therefore with a reduced data volume. Provision is then made in the image generation unit for transferring the resolution of the first projection measurement data record onto the at least one second projection measurement data record with reduced resolution and/or onto an image data record which is based on the at least one second projection measurement data record with reduced resolution. Therefore, for a spectral image data record which is based on the first and the at least one second projection measurement data record, a resolution is achieved which corresponds to the first projection measurement data record, such that high-resolution spectral image data can be obtained despite the reduction in the volume of data that is transferred between the detector and the image generation unit.

At least one embodiment of the inventive image generation system comprises a quantum counting detector having a plurality of energy thresholds for capturing spectrally resolved projection measurement data from an examination region of a patient. The spectrally resolved projection measurement data comprises a first projection measurement data record, which is assigned to a first energy threshold, and at least one second projection measurement data record, which is assigned to at least one second energy threshold. A further part of the inventive image generation system is a data reduction unit for generating at least one second projection measurement data record with reduced resolution on the basis of the at least one second projection measurement data record. As mentioned above, the data reduction unit is arranged in a detector-based manner.

At least one embodiment of the inventive image generation system further comprises a data transmission unit for transmitting the projection measurement data from the quantum counting detector to an image generation unit. Such a data transmission unit may comprise a data line, a slip ring for transferring the data between the detector and the stationary part of the image generation system, or a wireless transfer system, for example.

At least one embodiment of the inventive image generation system further comprises an image generation unit for transferring the resolution of the first projection measurement data record onto the at least one second projection measurement data record with reduced resolution and/or onto an image data record which is based on the at least one second projection measurement data record with reduced resolution. Furthermore, the image generation unit is configured to reconstruct image data on the basis of the transmitted projection measurement data. The transfer of the resolution can take place before the reconstruction of the image data, but can also take place between individual steps of the image reconstruction.

At least one embodiment of the inventive computer tomography system has an X-ray source for irradiating an examination region of a patient with polychromatic X-radiation and at least one embodiment of an inventive image generation system.

A number of important components of at least one embodiment of the inventive image generation system can be developed in the form of software components. This applies to the data reduction unit and the image generation unit in particular.

However, it is also possible in principle to realize some of these components in the form of software-assisted hardware, e.g. FPGAs or similar, particularly if very rapid calculations are required.

A largely software-based realization has the advantage that computer tomography systems which are already in use can also be upgraded easily via a software update in order to work in at least one embodiment of the inventive manner. In this respect, at least one embodiment of the invention is also achieved by a computer program product which can be loaded directly into a memory of a computer tomography system, with program code sections for executing all steps of the inventive method when the program is executed in the computer tomography system.

In addition to the computer program, such a computer program product may comprise additional elements if applicable, e.g. documentation and/or additional components including hardware components such as e.g. hardware keys (dongles etc.) for using the software.

For the purpose of transportation to the computer tomography system and/or storage at or in the computer tomography system, a computer-readable medium may be used such as e.g. a memory stick, a hard disk or other transportable or integral data storage medium on which are stored the program sections of the computer program that can be read in and executed by a computer unit. The computer unit may have e.g. a microprocessor or a plurality of microprocessors working together for this purpose, or similar. A wireless transfer of the computer program is also possible.

BRIEF DESCRIPTION OF THE DRAWINGS

The invention is explained again in greater detail below with reference to example embodiments and the appended figures and, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the inventive method for generating CT image data with spectral information from an examination region of a patient, the examination region is exposed to polychromatic X-radiation. Spectrally resolved projection measurement data from the examination region is then captured via a photon counting detector having a plurality of energy thresholds. The spectrally resolved projection measurement data comprises a first projection measurement data record, which is assigned to a first energy threshold, and at least one second projection measurement data record, which is assigned to at least one second energy threshold.

On the basis of the at least one second projection measurement data record, at least one second projection measurement data record with reduced resolution is generated. This procedure takes place in a detector-based manner, i.e. in a data reduction unit which is attached to the detector and follows the movement of the detector. The first projection measurement data record and the at least one second projection measurement data record with reduced resolution are then transmitted to an image generation unit. The image generation unit is situated outside the system that follows the rotational movement of the gantry.

By virtue of at least one embodiment of the inventive method, the transfer of the projection measurement data records can advantageously be carried out at least partly with reduced resolution and therefore with a reduced data volume. Provision is then made in the image generation unit for transferring the resolution of the first projection measurement data record onto the at least one second projection measurement data record with reduced resolution and/or onto an image data record which is based on the at least one second projection measurement data record with reduced resolution. Therefore, for a spectral image data record which is based on the first and the at least one second projection measurement data record, a resolution is achieved which corresponds to the first projection measurement data record, such that high-resolution spectral image data can be obtained despite the reduction in the volume of data that is transferred between the detector and the image generation unit.

At least one embodiment of the inventive image generation system comprises a quantum counting detector having a plurality of energy thresholds for capturing spectrally resolved projection measurement data from an examination region of a patient. The spectrally resolved projection measurement data comprises a first projection measurement data record, which is assigned to a first energy threshold, and at least one second projection measurement data record, which is assigned to at least one second energy threshold. A further part of the inventive image generation system is a data reduction unit for generating at least one second projection measurement data record with reduced resolution on the basis of the at least one second projection measurement data record. As mentioned above, the data reduction unit is arranged in a detector-based manner.

At least one embodiment of the inventive image generation system further comprises a data transmission unit for transmitting the projection measurement data from the quantum counting detector to an image generation unit. Such a data transmission unit may comprise a data line, a slip ring for transferring the data between the detector and the stationary part of the image generation system, or a wireless transfer system, for example.

At least one embodiment of the inventive image generation system further comprises an image generation unit for transferring the resolution of the first projection measurement data record onto the at least one second projection measurement data record with reduced resolution and/or onto an image data record which is based on the at least one second projection measurement data record with reduced resolution. Furthermore, the image generation unit is configured to reconstruct image data on the basis of the transmitted projection measurement data. The transfer of the resolution can take place before the reconstruction of the image data, but can also take place between individual steps of the image reconstruction.

At least one embodiment of the inventive computer tomography system has an X-ray source for irradiating an examination region of a patient with polychromatic X-radiation and at least one embodiment of an inventive image generation system.

A number of important components of at least one embodiment of the inventive image generation system can be developed in the form of software components. This applies to the data reduction unit and the image generation unit in particular.

However, it is also possible in principle to realize some of these components in the form of software-assisted hardware, e.g. FPGAs or similar, particularly if very rapid calculations are required.

A largely software-based realization has the advantage that computer tomography systems which are already in use can also be upgraded easily via a software update in order to work in at least one embodiment of the inventive manner. In this respect, at least one embodiment of the invention is also achieved by a computer program product which can be loaded directly into a memory of a computer tomography system, with program code sections for executing all steps of the inventive method when the program is executed in the computer tomography system.

In addition to the computer program, such a computer program product may comprise additional elements if applicable, e.g. documentation and/or additional components including hardware components such as e.g. hardware keys (dongles etc.) for using the software.

For the purpose of transportation to the computer tomography system and/or storage at or in the computer tomography system, a computer-readable medium may be used such as e.g. a memory stick, a hard disk or other transportable or integral data storage medium on which are stored the program sections of the computer program that can be read in and executed by a computer unit. The computer unit may have e.g. a microprocessor or a plurality of microprocessors working together for this purpose, or similar. A wireless transfer of the computer program is also possible.

The claims and the following description each contain particularly advantageous embodiments and developments of the invention. In this case, it is possible in particular to develop the claims from one class of claim in the same way as the dependent claims from another class of claim and their associated description parts. Moreover, the various features of different example embodiments and claims can also be combined in the context of the invention to produce further example embodiments.

In an embodiment of the inventive method for generating CT image data with spectral information from an examination region of a patient, a combination image is generated. In order to achieve this, a first image data record and at least one second image data record are reconstructed on the basis of the first projection measurement data record and on the basis of the at least one second projection measurement data record with reduced resolution. This procedure takes place by applying the transfer of the resolution of the first projection measurement data record onto the at least one second projection measurement data record with reduced resolution and/or onto the at least one second image data record.

A combination image is then generated by combining the first image data record and the at least one second image data record. The combination image can be generated e.g. by subtraction or weighted addition of individual image data records, i.e. in particular the first and the at least one second image data record. Such a combination image can be used e.g. for contrast-amplified representation of individual types of material, e.g. iodine or bone material. Using the inventive method, this combination image can advantageously be generated with high resolution despite a reduction in the volume of data to be transferred.

In a preferred embodiment of the inventive method for generating CT image data with spectral information from an examination region of a patient, the first energy threshold has a lower energy value than the at least one second energy threshold. In this embodiment, the first projection measurement data record comprises the greatest volume of structural information and is therefore transferred with its resolution unchanged. By comparison, projection measurement data which is assigned to the at least one second energy threshold is transferred with reduced resolution and subsequently receives structural information from the first projection measurement data record. Using this approach, it is possible to achieve an optimal resolution of structural details combined with a reduction in the volume of data to be transferred.

In a variant embodiment of the inventive method for generating CT image data with spectral information from an examination region of a patient, the reduced resolution of the at least one second projection measurement data record is generated by reducing the resolution in at least one of the following directions of the detector:
  in channel direction,
  in line direction,
  in projection direction.

The line direction of a detector usually runs in a z-direction, i.e. in the direction of the system axis of a CT system. The channel direction runs orthogonally to the line direction and tangentially to the detector surface. By comparison, the projection direction runs orthogonally to the detector surface and hence also orthogonally to the line direction and to the channel direction.

A particularly reduced resolution of the at least one second projection measurement data record can be achieved by reducing the resolution in channel direction, line direction and projection direction concurrently.

In the context of at least one embodiment of the inventive method for generating CT image data with spectral information from an examination region of a patient, the first projection measurement data record can also be acquired using a shorter frame time than the at least one second projection measurement data record. This makes allowance for the higher resolution with which the first projection measurement data record is transferred. Due to the movement of the detector during the acquisition of the projection measurement data, loss of sharpness (blurring) occurs as a function of the frame time, and therefore the increased resolution of the photon counting detector can only be used efficiently if the frame time, i.e. the time in which an image recording of the examination region from a given direction takes place, is shortened accordingly. An image recording of particularly good quality is therefore advantageously achieved when using this variant.

In an embodiment of the inventive method for generating CT image data with spectral information from an examination region of a patient, the transfer of the higher resolution can take place using a band filter. Regularization of the transfer via gradient comparison can be beneficial here. Using the gradient term, it is possible subsequently to recover a difference in the X-ray hardness for different energy thresholds and the associated contrasts, which is lost during the transfer of the resolution from the first energy threshold onto higher energy thresholds.

The transfer of the higher resolution can take place as part of the generation of the image data in one of the following process stages, for example:

before or after preprocessing of the projection measurement data, after a projection-based material breakdown or another spectral application, before or after back-projection of the projection measurement data, after an image-based material breakdown or another spectral application, during one of the steps of a material breakdown or another spectral application via iterative reconstruction.

Therefore the resolution transfer can advantageously take place in various process stages as required.

In a preferred embodiment of the inventive method for generating CT image data with spectral information from an examination region of a patient, the following approach is used for the purpose of transferring the resolution of the first projection measurement data record onto the at least one second projection measurement data record with reduced resolution and/or onto an image data record which is based on the at least one second projection measurement data record with reduced resolution: Firstly, a first projection measurement data record with reduced resolution is generated on the basis of the first projection measurement data record. Next, higher resolution difference data is generated on the basis of a subtraction of the first projection measurement data record and the first projection measurement data record with reduced resolution. Finally, the higher resolution difference data, possibly multiplied by a normalization factor comprising a quotient from the second projection measurement data record with reduced resolution and the first projection measurement data record with reduced resolution, is added to the second projection measurement data record with reduced resolution. In this way, a second projection measurement data record with increased resolution is recreated, and can be combined with the first projection measurement data record to generate a higher resolution image comprising spectral information.

Figure 1:
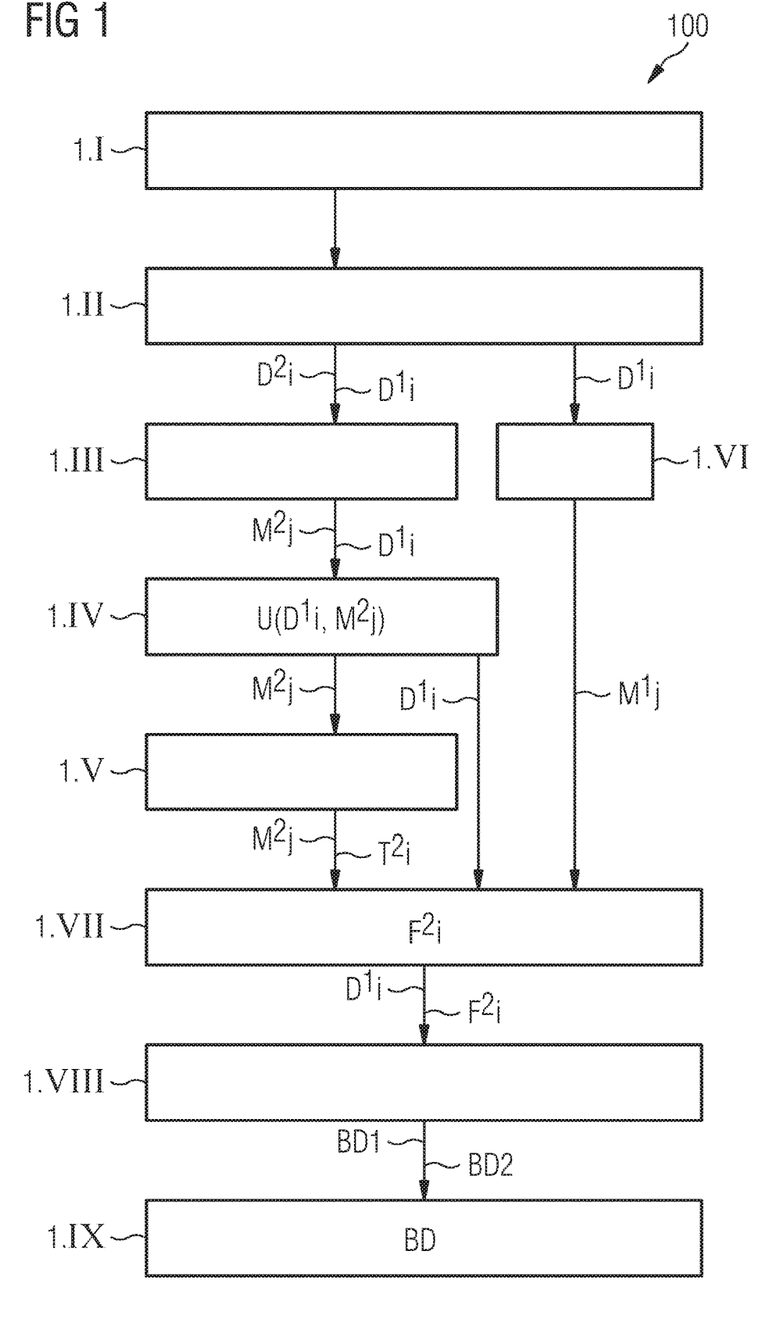
FIG. 1 shows a flow diagram which illustrates a method for generating CT image data with spectral information from an examination region of a patient according to an example embodiment of the invention.

FIG. 1 shows a flow diagram 100 which illustrates individual steps of a method for generating CT image data with spectral information from an examination region of a patient according to an example embodiment of the invention. Individual steps of the method shown in FIG. 1 are graphically illustrated in FIG. 2 and FIG. 3 with the aid of bar charts. In the step 1.I an examination region is initially exposed to X-radiation in the context of a CT image recording. In the step 1.II, spectrally resolved projection measurement data $D^1_i$, $D^2_i$ from the examination region is then captured with the aid of a photon counting detector having a plurality of energy thresholds.

During this procedure, first and second projection measurement data $D^1_i$, $D^2_i$ is captured, these being assigned to different energy thresholds of the X-ray detector. The index i in this case signifies different channels, to which different pixels or subpixels are assigned and via which an image region to be captured by the detector is simultaneously captured. By comparison, the superscript index 1 or 2 signifies the assignment of the first projection measurement data $D^1_i$ to the first energy threshold and the second projection measurement data $D^2_i$ to the second energy threshold.

Figure 2:
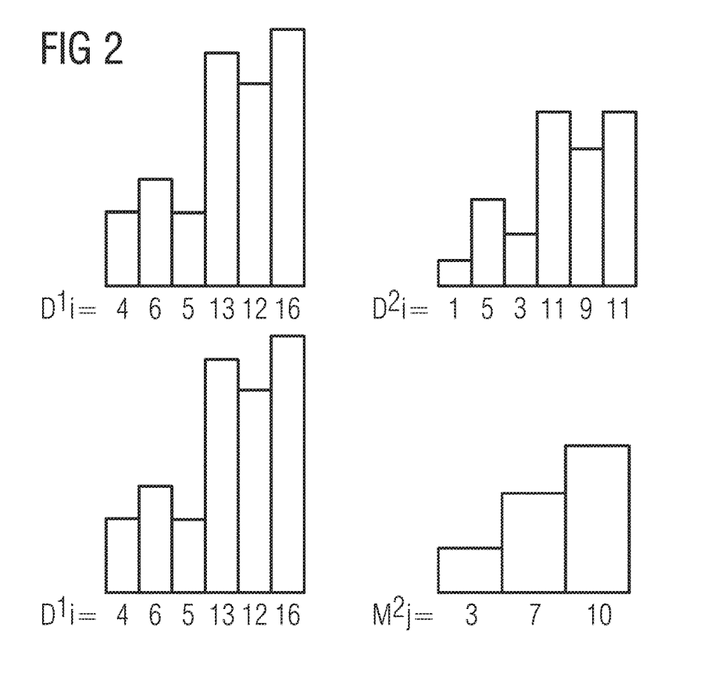
FIG. 2 shows a schematic representation of projection measurement data which has been captured and projection measurement data whose resolution has been reduced.

For the sake of clarity, FIG. 2 shows this procedure for 6 channels (i=0 to 5) and two energy thresholds. Each of the channels is assigned one bar of a bar chart. At the top left of FIG. 2, the first projection measurement data $D^1_i$ for the first threshold is represented. For this purpose, the individual channels are assigned different count rates which correspond to the different attenuations of the X-rays captured at different locations. For example, a first channel has a count rate $D^1_0=4$, a second channel has a count rate $D^1_0=6$, etc.

At the top right of FIG. 2, the count rates for different channels are represented for the second projection measurement data $D^2_i$ for the second energy threshold. For this purpose, the individual channels are assigned different count rates which correspond to the different attenuations of the X-rays captured at different locations. For example, a first channel has a count rate $D^2_0=1$, a second channel has a count rate $D^1_0=5$ etc. It is worth noting that the count rates for the individual channels of the second projection measurement data $D^2_0$ are lower than the count rates of the corresponding channels of the first projection measurement data $D^1_0$. This is because the first energy threshold is lower than the second energy threshold, and therefore some of the X-ray quanta that are still detected when using the first energy threshold lie below the second energy threshold and are no longer captured during the acquisition of the second projection measurement data.

According to the method illustrated in FIG. 1, in the step 1.III the first projection measurement data $D^1_i$ as captured using the lowest energy threshold is left in its full resolution, while the second projection measurement data $D^2_i$ as captured using the higher energy threshold is converted into an auxiliary quantity, subsequently referred to as the second weaker resolution projection measurement data $M^2_j$. This procedure is illustrated in FIG. 2 by the two lower diagrams. Shown again at the bottom left of FIG. 2 is the first projection measurement data $D^1_i$ for six channels, which was captured during the step 1.II and did not change in the step 1.III. Shown at the bottom right of FIG. 2 is the comparatively weaker resolution projection measurement data $M^2_j$ for j=0 to 2, which was generated on the basis of the second projection measurement data $D^2_i$. The generated weaker resolution projection measurement data $M^2_j$ is averaged over two channels in each case, i.e.

$$M^2_j = \frac{D^2_{2j} + D^2_{2j+1}}{2}, \; j\varepsilon\{0 \ldots N/2 - 1\},$$

where N is a whole number and N=5 in the example shown in FIG. 2.

All of the steps cited above are performed in a detector-based manner, i.e. either in the detector or in a computing unit which rotates with the detector. In the step 1.IV, both the higher resolution first projection measurement data $D^1_i$ and the weaker resolution projection measurement data $M^2_j$ are transmitted $U(D^1_i, M^2_j)$ to an image generation unit which is separate from the detector and is preferably permanently installed in a control entity of the CT system concerned. Since the resolution of the second projection measurement data $D^2_i$ was reduced, the data transfer rate when transmitting the projection measurement data $D^1_i$, $M^2_j$ can now be lower.

Figure 3:
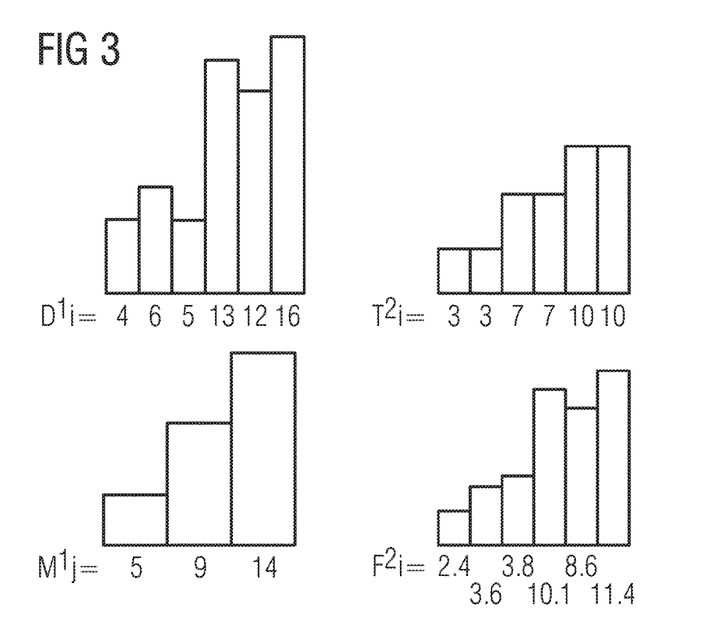
FIG. 3 shows a schematic representation of a transfer of the resolution of higher resolution projection measurement data onto lower resolution projection measurement data.

In the step 1.V, an auxiliary quantity $T^2_i$ having the same channel number as the higher resolution first projection measurement data $D^1_i$ is then determined on the basis of the weaker resolution projection measurement data $M^2_j$. The auxiliary quantity $T^2_i$ is produced as follows:

$$T_i^2 = M_{floor(i/2)}^2, i\varepsilon\{0 \ldots N-1\}$$

where N=5 in the example shown in FIG. 3, and "floor" is a rounding function which rounds a number down to the next whole number. It can be seen from the part-drawing at the top right of FIG. 3 that the values of the weaker resolution projection measurement data $M^2_j$ were simply retained for the purpose of generating the auxiliary quantity $T^2_i$ and the number of channels was doubled. In this case, an additional channel was simply added to each of the three channels of the weaker resolution projection measurement data $M^2_j$, and was given the same count rate value as the existing channel.

In the step 1.VI, a further auxiliary quantity, subsequently referred to as weaker resolution first projection measurement data $M^1_j$, is calculated on the basis of the first projection measurement data $D^1_i$, wherein the resolution of the auxiliary quantity $M^1_j$ is halved in comparison with the resolution of the first projection measurement data $D^1_i$. The first weaker resolution projection measurement data $M^1_j$ is derived as follows:

$$M_j^1 = \frac{D_{2j}^1 + D_{2j+1}^1}{2}, j\varepsilon\{0 \ldots N/2-1\}.$$

The weaker resolution first projection measurement data $M^1_j$ is illustrated at the bottom left of FIG. 3. It can be seen there that the count rates of the channels 0, 1, 2 are simply average values of adjacent channels of the higher resolution projection measurement data $D^1_i$.

In the step 1.VII, corrected high-resolution second projection measurement data $F^2_i$ is then produced, enriched by the structure information of the first projection measurement data $D^1_i$. The corrected high-resolution second projection measurement data $F^2_i$ is derived as follows:

$$F_i^2 = \frac{M_{floor(i/2)}^2}{M_{floor(i/2)}^1}(D_i^1 - M_{floor(i/2)}^1) + T_i^2, i\varepsilon\{0 \ldots N-1\}.$$

The transfer of the structure information of the high-resolution first projection measurement data $D^1_i$ is effected by adding the difference between the first high-resolution projection measurement data $D^1_i$ and the low-resolution first projection measurement data $M^1_{floor(i/2)}$, this difference being again normalized using the quotient from the two auxiliary quantities $M^2_{floor(i/2)}$ and $M^1_{floor(i/2)}$.

In the step 1.VIII, image data records BD1, BD2 assigned to different spectra are then reconstructed on the basis of the high-resolution first projection measurement data $D^1_i$ and the corrected high-resolution second projection measurement data $F^2_i$.

In the step 1.IX, a difference image BD is finally generated on the basis of the assigned image data records BD1, BD2.

It can be seen at the bottom right of FIG. 3 that the corrected high-resolution second projection measurement data $F^2_i$, enriched by the structure information of the first projection measurement data $D^1_i$, has an edge between channel 2 and channel 3 in a similar manner to the original second projection measurement data $D^2_i$, the count rate value between channel 2 and channel 3 increasing from 3.8 to 10.1. By comparison, the count rate value in the original second projection measurement data $D^2_i$ increases from 3 to 11 between channel 2 (third channel) and channel 3 (fourth channel). The significant increase in value may represent e.g. an edge which would otherwise be lost during the transfer of the low-resolution second projection measurement data $M^2_j$ between a rotating detector and a stationary evaluation unit which performs an image reconstruction function, for example. In this way, finer structure information in the second projection measurement data is reconstructed subsequently without having to transfer a larger volume of data during the data transfer.

Figure 4:
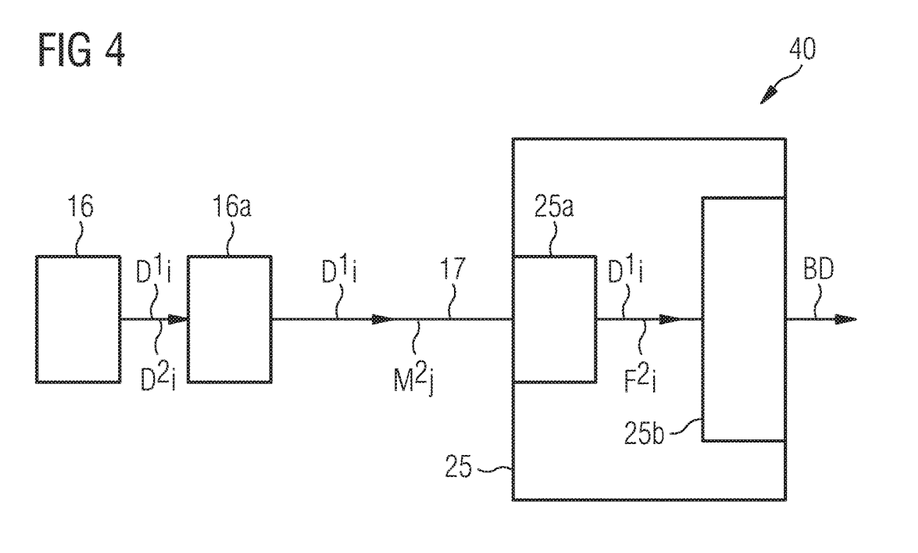
FIG. 4 shows a schematic representation of an image generation system according to an example embodiment of the invention.

FIG. 4 shows an image generation system 40 according to an example embodiment of the invention. The image generation system 40 comprises a quantum counting detector 16. The quantum counting detector 16 has a plurality of energy thresholds and captures spectrally resolved first and second projection measurement data $D^1_i$, $D^2_i$ from an examination region of a patient. Connected to the detector is a data reduction unit 16a, which is used to generate a projection measurement data record $M^2_j$ with reduced resolution on the basis of a captured projection measurement data record $D^2_i$ that is assigned to a higher energy threshold. The projection measurement data record or records $M^2_j$ with reduced resolution and at least one projection measurement data record $D^1_i$ which does not have reduced resolution are transmitted with the aid of a data transmission unit 17 from the data reduction unit 16a to an image generation unit 25.

The data transmission unit can comprise e.g. a transfer line and a slip ring for transferring the projection measurement data $D^1_i$, $M^2_j$ from the rotating data reduction unit 16a to the stationary image generation unit 25. The image generation unit 25 can be part of a control entity of a CT system (see FIG. 5), for example, and has a transfer unit 25a which is used to transfer the resolution of the first projection measurement data record $D^1_i$, whose resolution has not been reduced, onto the second projection measurement data record $M^2_i$ with reduced resolution. Corrected second projection measurement data $F^2_i$ with increased resolution is generated in this way. The projection measurement data $D^1_i$, $F^2_i$ with high resolution is then transmitted to an image reconstruction unit 25b, which is used to reconstruct image data BD on the basis of the projection measurement data $D^1_i$, $F^2_i$.

Figure 5:
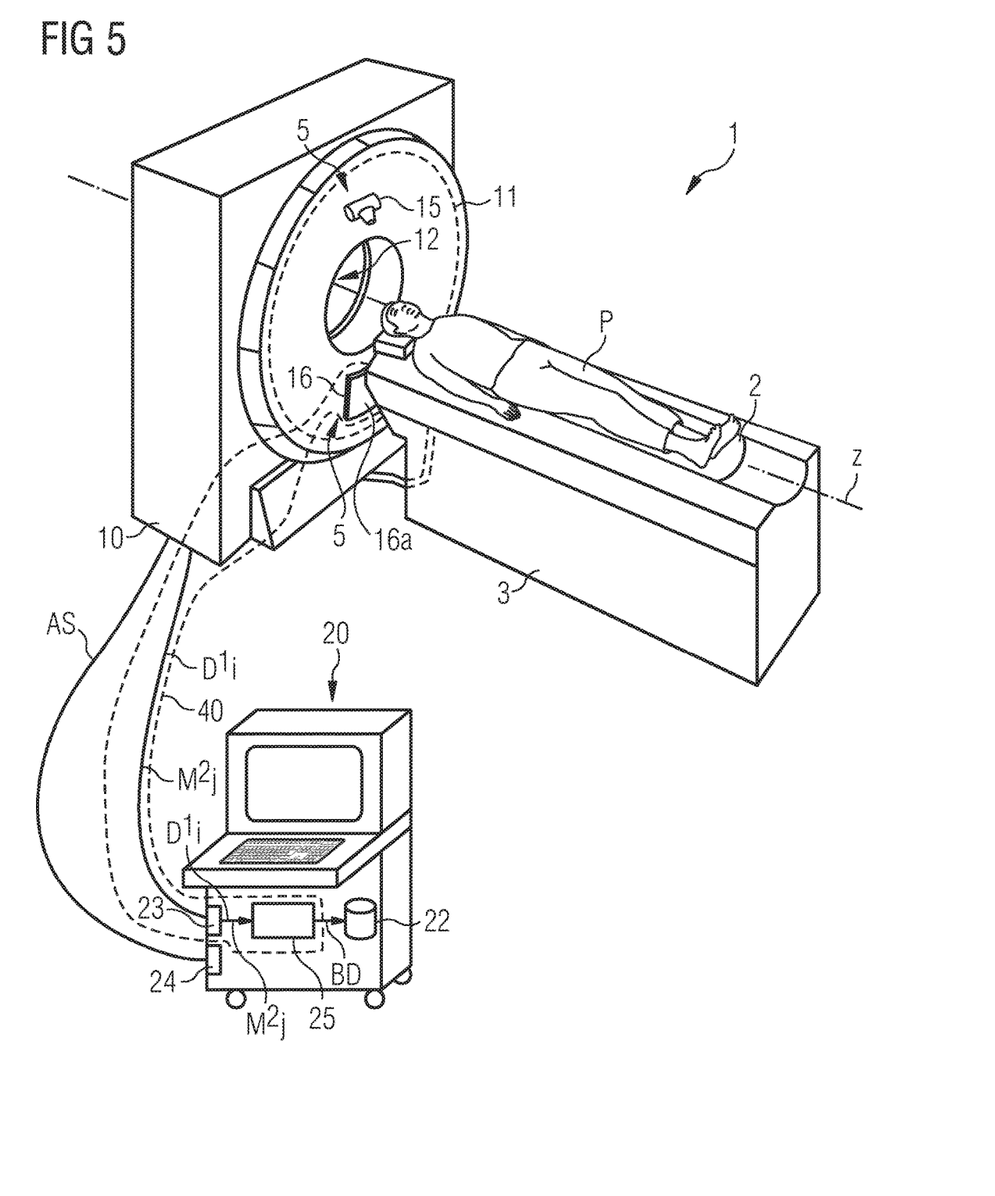
FIG. 5 shows a schematic representation of a computer tomography system according to an example embodiment of the invention.

FIG. 5 shows a computer tomography system 1 comprising the image generation system 40 shown in FIG. 4 (marked by a broken line in FIG. 5). The CT system 1 in this case consists essentially of a conventional scanning unit 10 in which a projection data acquisition unit 5, this comprising a spectrally resolving detector 16 and an X-ray source 15 which is arranged opposite the detector 16 and emits polychromatic X-rays, revolves around a measurement chamber 12 on a gantry 11. In front of the scanning unit 10 is situated a patient support entity 3 or patient couch 3, whose upper part 2 and a patient P positioned thereon can be displaced towards the scanning unit 10 in order to move the patient P through the measurement chamber 12 relative to the detector system 16.

The scanning unit 10 and the patient couch 3 are controlled by a control entity 20, from which acquisition control signals AS are received via a conventional control interface 24 in order to control the overall system according to predefined measuring protocols in the usual manner. In the case of spiral acquisition, a helical path is produced as a result of the patient P moving along the z-direction, which corresponds to the system axis z extending through the measurement chamber 12, and the concurrent rotation of the X-ray source 15 for the X-ray source 15 relative to the patient P during the measurement.

The detector 16 is situated opposite the X-ray source 15 and continuously follows the movement thereof in order to capture spectrally resolved projection measurement data $D^2_i$, which is then used to reconstruct volume image data and/or layer image data. It is likewise possible to perform a sequential measuring method, in which a fixed position in z-direction is selected and the necessary spectrally resolved projection measurement data $D^1_i$, $D^2_i$ is then captured during a rotation, a partial rotation or a plurality of rotations at the z-position concerned in order to reconstruct a sectional image at this z-position or to reconstruct image data from the projection measurement data $D^1_i$, $D^2_i$ of a plurality of z-positions.

An embodiment of the inventive method can also be used with other CT systems in principle, e.g. using a plurality of X-ray sources and/or detectors and/or using a detector which forms a complete ring. For example, an embodiment of the inventive method can also be applied to a system which has a fixed couch and a gantry which moves in a z-direction (a so-called sliding gantry).

The projection measurement data $D^1_i$, $D^2_i$ (also referred to a raw data in the following) acquired by the detector 16 is reduced by a data reduction unit 16a adjacent to the detector as described above and projection measurement data $D^1_i$, $M^2_i$ is forwarded to the control entity 20 via a data interface 23. This projection measurement data $D^1_i$, $M^2_i$ is then, possibly after suitable preprocessing (e.g. filtering and/or ray hardening correction), further processed in an image generation unit 25 which in this example embodiment is realized in the form of software on a processor in the control entity 20. By use of this image generation unit 25, the previously reduced resolution of the second projection measurement data $M^2_i$ is increased again in the manner illustrated in FIG. 1, and image data BD is reconstructed on the basis of the high-resolution projection measurement data with the aid of a reconstruction method. For example, a reconstruction method based on filtered back-projection can be used as a reconstruction method.

The generated image data is then stored in a memory 22 of the control entity 20 and/or output on the display screen of the control entity 20 in the usual manner. It can also be supplied to a network such as e.g. a radiological information system (RIS) which is connected to the computer tomography system 1 via an interface (not shown in FIG. 5) and stored in a mass memory which can be accessed there or output as images on printers or filming stations connected thereto. The data can therefore be further processed and then stored or output as desired.

Components of the image generation system 40 may be realized primarily or completely in the form of software elements on a suitable processor. In particular, the interfaces between individual components, e.g. between components 25a, 25b of the image generation unit 25, may likewise be designed purely in the form of software. It is merely necessary to grant access permissions to appropriate storage areas in which the data is meanwhile stored in an appropriate manner and can be retrieved and updated at any time.

In conclusion, it is again noted that the method and devices described above are merely preferred example embodiments of the invention and that the invention may be varied by a person skilled in the art without thereby departing from the scope of the invention as defined by the claims. For the sake of completeness, it is also noted that use of the indefinite article "a" or "an" does not preclude the possibility of multiple instances of the features concerned. Likewise, the term "unit" does not preclude the possibility that this may consist of a plurality of components, which may also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating CT image data with spectral information from an examination region of a patient, the method comprising:
   exposing the examination region to polychromatic X-radiation;
   capturing spectrally resolved projection measurement data from the examination region, via a photon counting detector including a plurality of energy thresholds, wherein the spectrally resolved projection measurement data includes a first projection measurement data record assigned to a first energy threshold, and at least one second projection measurement data record assigned to at least one second energy threshold;
   generating at least one second projection measurement data record with reduced resolution based upon the at least one second projection measurement data record;
   transmitting the first projection measurement data record and the at least one second projection measurement data record with reduced resolution to an image generation unit; and
   transferring a higher resolution of the first projection measurement data record onto at least one of
      the at least one second projection measurement data record with reduced resolution and an image data record, based on the at least one second projection measurement data record with reduced resolution.

2. The method of claim 1, wherein a combination image is generated by at least:
reconstructing a first image data record and at least one second image data record based upon the first projection measurement data record and based upon the at least one second projection measurement data record with reduced resolution,
applying the transfer of the resolution of the first projection measurement data record onto at least one of
the at least one second projection measurement data record with reduced resolution and
the at least one second image data record, and
generating the combination image by combining the first image data record and the at least one second image data record.

3. The method of claim 1, wherein the first energy threshold has a lower energy value than the at least one second energy threshold.

4. The method of claim 1, wherein the reduced resolution of the at least one second projection measurement data record with reduced resolution is generated by reducing the resolution in at least one of the following directions of the detector:
in channel direction,
in line direction, or
in projection direction.

5. The method of claim 4, wherein the reduced resolution of the at least one second projection measurement data record is achieved by reducing the resolution in channel direction, line direction and projection direction.

6. The method of claim 1, wherein the first projection measurement data record is acquired using a shorter frame time than the at least one second projection measurement data record.

7. The method of claim 1, wherein the transfer of the higher resolution takes place using a band filter.

8. The method of claim 7, wherein regularization of the higher resolution is carried out by way of gradient comparison.

9. The method of claim 1, wherein the transfer of the higher resolution takes place as part of the generation of the image data in one of the following:
before preprocessing of the projection measurement data,
before back-projection of the projection measurement data,
after the back-projection of the projection measurement data, or
after a material breakdown of the projection measurement data or image data.

10. The method of claim 1, wherein the following are performed in transferring the resolution of the first projection measurement data record onto at least one of the at least one second projection measurement data record with reduced resolution and an image data record based on the at least one second projection measurement data record with reduced resolution:
determining a first projection measurement data record with reduced resolution based upon the first projection measurement data record,
determining higher resolution difference data based on a subtraction of the first projection measurement data record and the first projection measurement data record with reduced resolution, and
adding the higher resolution difference data to the second projection measurement data record with reduced resolution.

11. An image generation system, comprising:
a quantum counting detector, including a plurality of energy thresholds, to capture spectrally resolved projection measurement data from an examination region of a patient, the spectrally resolved projection measurement data including a first projection measurement data record assigned to a first energy threshold, and at least one second projection measurement data record assigned to at least one second energy threshold;
a data reduction unit to generate at least one second projection measurement data record with reduced resolution based upon the at least one second projection measurement data record;
a data transmission unit to transmit the projection measurement data from the quantum counting detector to an image generation unit, the image generation unit transfers the resolution of the first projection measurement data record onto at least one of the at least one second projection measurement data record with reduced resolution and an image data record based upon the at least one second projection measurement data record with reduced resolution, and reconstructs image data based on the transmitted projection measurement data.

12. A computer tomography system comprising:
an X-ray source to irradiate the examination region of the patient with polychromatic X-radiation; and
the image generation system of claim 11.

13. A non-transitory computer program product comprising a computer program, directly loadable into a memory device of a computer tomography system, including program sections to execute the method of claim 1 when the computer program is executed in the computer tomography system.

14. A non-transitory computer-readable medium, on which are stored program sections, readable into and executable by a computer unit, to execute the method of claim 1 when the program sections are executed by the computer unit.

15. The method of claim 2, wherein the first energy threshold has a relatively lower energy value than the at least one second energy threshold.

16. The method of claim 2, wherein the reduced resolution of the at least one second projection measurement data record with reduced resolution is generated by reducing the resolution in at least one of the following directions of the detector:
in channel direction,
in line direction, or
in projection direction.

17. The method of claim 16, wherein the reduced resolution of the at least one second projection measurement data record is achieved by reducing the resolution in channel direction, line direction and projection direction.

18. The method of claim 2, wherein the transfer of the higher resolution takes place using a band filter.

19. The method of claim 18, wherein regularization of the higher resolution is carried out by way of gradient comparison.

20. A non-transitory computer-readable medium, on which are stored program sections, readable into and executable by a computer unit, to execute the method of claim 2 when the program sections are executed by the computer unit.

\* \* \* \* \*